United States Patent [19]

McCabe et al.

[11] Patent Number: 5,506,125

[45] Date of Patent: Apr. 9, 1996

[54] GENE DELIVERY INSTRUMENT WITH REPLACEABLE CARTRIDGES

[75] Inventors: Dennis E. McCabe, Middleton; Richard J. Heinzen, North Freedom, both of Wis.

[73] Assignee: Agracetus, Inc., Middleton, Wis.

[21] Appl. No.: 172,447

[22] Filed: Dec. 22, 1993

[51] Int. Cl.[6] .................................. C12N 5/10; C12M 1/00
[52] U.S. Cl. .................................. 435/172.1; 435/285.1; 435/285.2; 435/285.3; 935/52; 935/85
[58] Field of Search ......................... 435/287, 172.1, 435/172.2, 172.3, 313; 935/52, 53, 85; 604/68–70, 72, 140, 141, 146; 128/24 EL; 73/12, 167; 239/81; 137/467, 527, 527.2, 527.4; 251/298; 210/447; 55/503

[56] References Cited

U.S. PATENT DOCUMENTS

| | | | |
|---|---|---|---|
| 3,788,484 | 1/1974 | Godin | 210/447 |
| 3,856,277 | 12/1974 | Tiramani | 210/447 |
| 4,376,053 | 3/1983 | Bullock et al. | 210/447 |
| 4,945,050 | 7/1990 | Sanford et al. | 435/172.1 |
| 5,015,580 | 5/1991 | Christou et al. | 435/172.3 |
| 5,120,657 | 6/1992 | McCabe et al. | 435/287 |
| 5,141,020 | 8/1992 | Sunderhaus et al. | 137/467 |
| 5,149,655 | 9/1992 | McCabe et al. | 435/287 |
| 5,204,253 | 4/1993 | Sanford et al. | 435/172.3 |

OTHER PUBLICATIONS

Finer, et al., "Development of the particle inflow gun for DNA delivery to plant cells," *Plant Cell Reports*, 11:323–328 (1992).

Iida, A., et al., "Gene delivery into cultured plant cells by DNA-coated gold particles accelerated by a pneumatic particle gun," *Theor. Appl. Genet.* 80:813–816 (1990).

Oard, et al., "Transient Gene Expression in Maize, Rice, and Wheat Cells Using an Airgun Apparatus," *Plant Physiol.*, 92:334–339 (1990).

Takeuchi, et al., "Plant transformation: a simple particle bombardment device based on flowing helium," *Plant Molecular Biology* 18:835–839 (1992).

Johnston, S. A. "Biolistic Transformation, Microbes to Mice," *Nature* 346:776–777 (1990).

Sanford, John C., "The biolistic process," *Tibtech* vol. 6 (1988).

Sanford, et al., "Delivery of Substances into Cells and Tissues Using a Particle Bombardment Process," *Particulate Science and Technology* 5:27–37 (1987).

Primary Examiner—William H. Beisner
Attorney, Agent, or Firm—Quarles & Brady

[57] ABSTRACT

An apparatus for acceleration of carrier particles into a target organism which may be used for rapid, sequential particle acceleration procedures comprises a holder for removable mounting cartridges. A first removable mounting cartridge detachably holds a carrier sheet coated with carrier particles which have themselves been coated with biological material. A second removable mounting cartridge comprises a retaining screen. The mounting cartridges may be inserted into the holder before particle acceleration and replaced quickly afterwards, thereby readying the apparatus for another particle acceleration. Convenient replacement of these consumable items eliminates the need to disassemble the apparatus between each particle acceleration procedure.

13 Claims, 4 Drawing Sheets

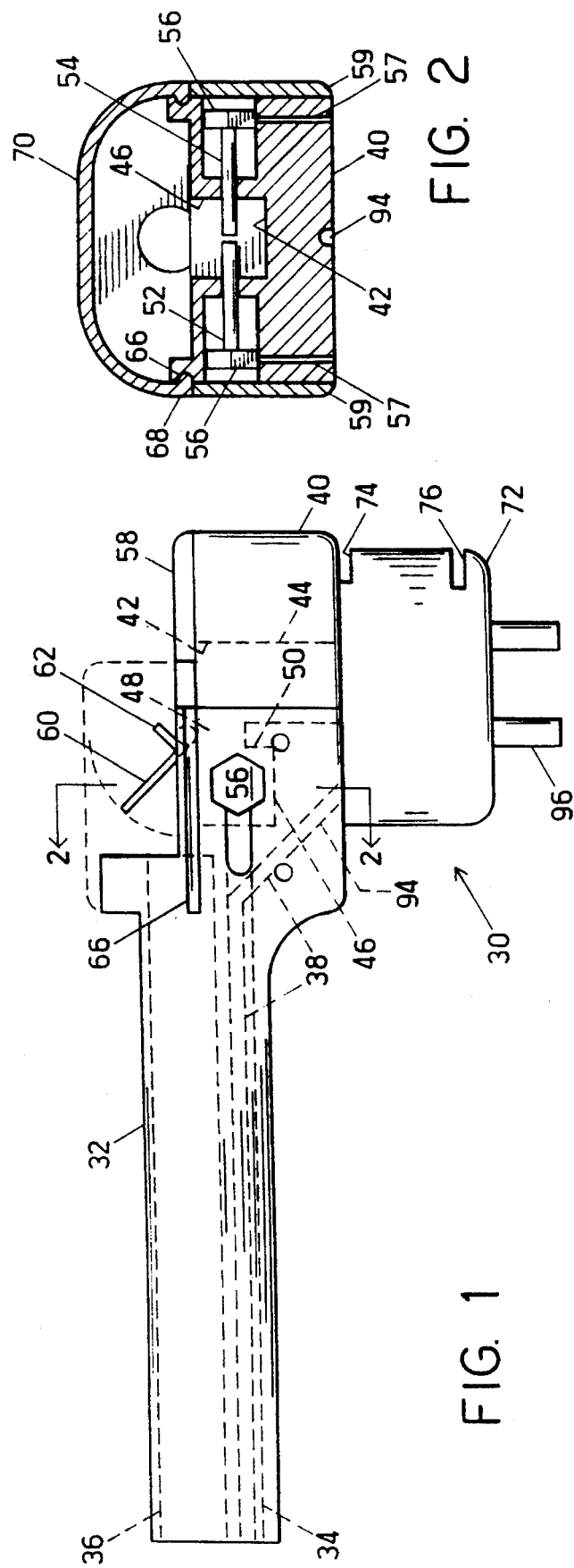

GENE DELIVERY INSTRUMENT WITH REPLACEABLE CARTRIDGES

FIELD OF THE INVENTION

The present invention relates to the field of gene transfer by particle acceleration, and in particular to a gene delivery instrument that facilitates rapid, repetitive sample loading, thereby increasing the rate at which a series of samples for particle acceleration may be delivered into a target animal, plant, cell, or tissue.

BACKGROUND OF THE INVENTION

There is much interest in the general field of the genetic engineering of living organisms. In the genetic engineering of an organism, foreign genetic material, typically a DNA vector constructed so as to express a suitable gene product in the cells of the target organism, is transferred into the genetic material of cells of the organism, through one of a variety of processes. In the past, the transformation techniques have varied widely from organism to organism, and few genetic transformation techniques have been developed which seem applicable to a large number of different organisms in different biological classes or kingdoms. Some of the prior art mechanisms utilized for inserting genetic material into living tissues include direct micro-injection; electroporation, a technique in which individual cells are subjected to an electric shock to cause those cells to take up DNA from a surrounding fluid; liposome-mediated transformations, in which DNA or other genetic material is encapsulated in bilipid vesicles which have an affinity to the cell walls of target organisms; and certain specific types of biological vectors or carriers which have the ability to transfect genetic material carried within them into certain specific target organisms, such as the plant transformation vector Agrobacterium tumefaciens and retroviral vectors which are used in animal hosts.

One technique exists which seems applicable to a wide range of target organisms. This technique is referred to as particle-mediated genetic transformation. In this technique, the genetic material, be it RNA or DNA, is coated onto small carrier particles. The carrier particles are then physically accelerated into the tissue which is to be transformed. For the process to work, the carrier particles are selected to be small enough so that they may be hurled through the walls and into the interior of cells of the target organism, without causing injury or significant harm to those cells. Several articles have been published describing the techniques and the apparatus utilized in such a particle-mediated transformation technique. Klein et al., "High-Velocity Microprojectiles for Delivering Nucleic Acids into Living Cells," *Nature* 327:70–73 (1987); and Sanford, "The Biolistic Process," *TIBTECH*, 6:299–302 (1988). Sanford and Klein, who are early investigators of particle-mediated transformation techniques, utilized a macro-projectile to accelerate the small carrier or micro-particles. The macro-projectile or macro-particle used by Sanford and Wolfe was literally a bullet fired by a ballistic shell which was, in actual fact, a firearm cartridge. The use of such extremely high velocity acceleration techniques required a large instrument, with very good shielding and a safety interlock, to prevent inadvertent harm to the experimenters.

A second technique developed for the acceleration of carrier particles carrying biological molecules into target cells for genetic transformations was based on a shock wave created by a high-voltage electric spark discharge. This apparatus, described in European published patent application number 270,356 and in U.S. Pat. No. 5,120,657, involves a pair of spaced electrodes placed on a spark discharge chamber. A high-voltage electric discharge is then passed between the electrodes to vaporize a water droplet placed between the electrodes. The spark discharge vaporizes the water droplet creating a shock wave, which accelerates a carrier sheet previously placed on the discharge chamber. The carrier sheet carries thereon the carrier particles, which have the biological genetic materials thereon. The carrier sheet is accelerated toward a retaining screen where the carrier sheet is stopped, the particles are separated from it, and only the carrier particles pass on into the biological tissues. The design for the particle acceleration apparatus as described in these publications was one which involved the desk top, or bench top, apparatus of relatively significant size and complexity and which was relatively immobile.

A smaller particle acceleration apparatus in which the operative portion of the device is hand-held is described in U.S. Pat. No. 5,149,655. The hand-held device permits the acceleration of particles carrying biological molecules into whole living organisms that are larger than can readily be placed onto a bench top unit.

The various particle acceleration techniques and devices described above were developed primarily for genetic transformation of individual cells and plant tissue. However, as the particle acceleration technology has developed, its use with laboratory and domestic animals has become an increasingly important aspect of the technology. Moreover, particle acceleration is proving to be well suited to developing genetic therapies and genetic vaccines in large animals and humans.

The underlying goal of particle acceleration is the efficient transfer, uptake and expression of foreign genetic material in a target animal, plant, cell, or tissue. Typically, the genetic material transferred is DNA encoding a peptide or protein absent from the target cells. The transferred DNA typically includes the necessary transcription and translation regulatory elements such as promoters, terminators, and ribosome binding sites, as required by a particular target host.

In plants, plant cells, and some animals much effort has been directed to obtaining germ-line transformants capable of constitutively or inducibly expressing a desirable gene product, and to transferring that capability to progeny plants grown from seed.

In contrast, the focus of more recent developments in human genetic therapy and vaccination has been the transient expression of transferred genes, either to provide a therapeutic protein to a somatic tissue, or to induce an immune response to the product of the transferred gene. This latter approach is now believed to offer dramatic advantages over conventional immunization protocols, for several reasons.

First, it will be dramatically less expensive to produce stable vaccines made of DNA than to produce peptide- or protein-based vaccines. Second, the ability to easily modify DNA will likely permit the production of customized vaccines. Third, as more and more genes encoding medically important antigens are discovered, it will be possible to generate vaccines against a vast array of infectious agents for which no vaccines are presently available. Finally, recent observations indicate that particle acceleration of DNA into human skin or mucosal tissue is particularly well suited to inducing a long-lasting immune response. As such, rapid, needle-free, painless, non-invasive vaccination will be facilitated by bringing the principles of particle acceleration to bear upon the epidemiological problems of vaccinating large populations against an array of infectious agents.

As a result of the direction in which the particle acceleration technology has developed, the ability to deliver samples in rapid succession is now required. Whereas the time between samples was relatively unimportant when the target was a plant cell suspension, when treating a number of human beings or large animals, it is desirable to complete the particle acceleration protocol as quickly as possible. Particularly with large animals, it is desirable to restrain the target animals for as short a time as possible. In existing particle acceleration devices, it has been necessary to disassemble at least a portion of the device between each use to install a fresh sample carrier sheet and to clean the retaining screen. This would result in an unacceptably long delay between samples.

In addition, the carrier sheet was attached directly to the discharge opening of earlier particle acceleration devices, typically by relying on the surface tension of a liquid such as oil or water. An additional source of delay between samples arose from the need to provide new liquid to attach each corner of the sheet.

It is, therefore, desirable to provide a safe and effective particle acceleration device which allows for reliable, rapid, repetitive delivery of genetic material into targets with minimal time between samples.

SUMMARY OF THE INVENTION

The present invention is summarized in that an apparatus useful for rapid sequential transfer of carrier particles coated with biological material and initially loaded onto a carrier sheet into a target organism comprises a holder for mounting cartridges having a first aperture adapted for removable insertion of the first mounting cartridge, the first mounting cartridge detachably holding the carrier sheet, the mounting cartridge holder further having a second aperture adapted for removable insertion of a second mounting cartridge, the second mounting cartridge comprising a retaining screen. In providing such a holder for mounting cartridges plus the mounting cartridges themselves, the apparatus of the present invention is an improvement over existing particle acceleration devices in that following each discharge the device is readily prepared for another discharge. A new carrier sheet, mounted in a new mounting cartridge is inserted, and the old carrier sheet; also embedded in the disposable cartridge, can be discarded. Similarly, a new retaining screen can be quickly inserted for the next discharge cycle. Insertion of a clean, or replacement retaining screen and a fresh carrier sheet may be accomplished in seconds rather than minutes that were previously required.

Moreover, this invention now enables one to prepare and store many samples before gene transfer by mounting a large number of carrier sheets into separate cartridges, such that many samples may be transformed quickly with only a short pause between samples.

It is an object of the present invention to provide an apparatus for particle acceleration which offers a shorter time between samples than existing devices.

It is a feature of the present invention that the carrier sheet and retaining screen are provided in easily insertible mounting cartridges which, when inserted, form a sample flight path bounded on its sides by the holder for the cartridges.

It is an advantage of the present invention that the apparatus is easily and quickly prepared between samples.

It is another advantage of the present invention that it facilitates rapid sequential sample handling in a manner heretofore unknown to the art.

BRIEF DESCRIPTION OF THE DRAWINGS

FIG. 1 is a side view of an embodiment of the present invention with certain parts omitted for clarity, showing a gene delivery instrument constructed in accordance with the present invention.

FIG. 2 is a sectional view of the body member of the apparatus of FIG. 1.

DESCRIPTION OF THE PREFERRED EMBODIMENT

The process of accelerating particles coated with biological material into target cells and organisms has been described in U.S. Pat. Nos. 5,120,657, and 5,149,655, the disclosures of which are incorporated herein by reference, and is here summarized, to clarify the purpose of the apparatus of the present invention.

Figure 8:
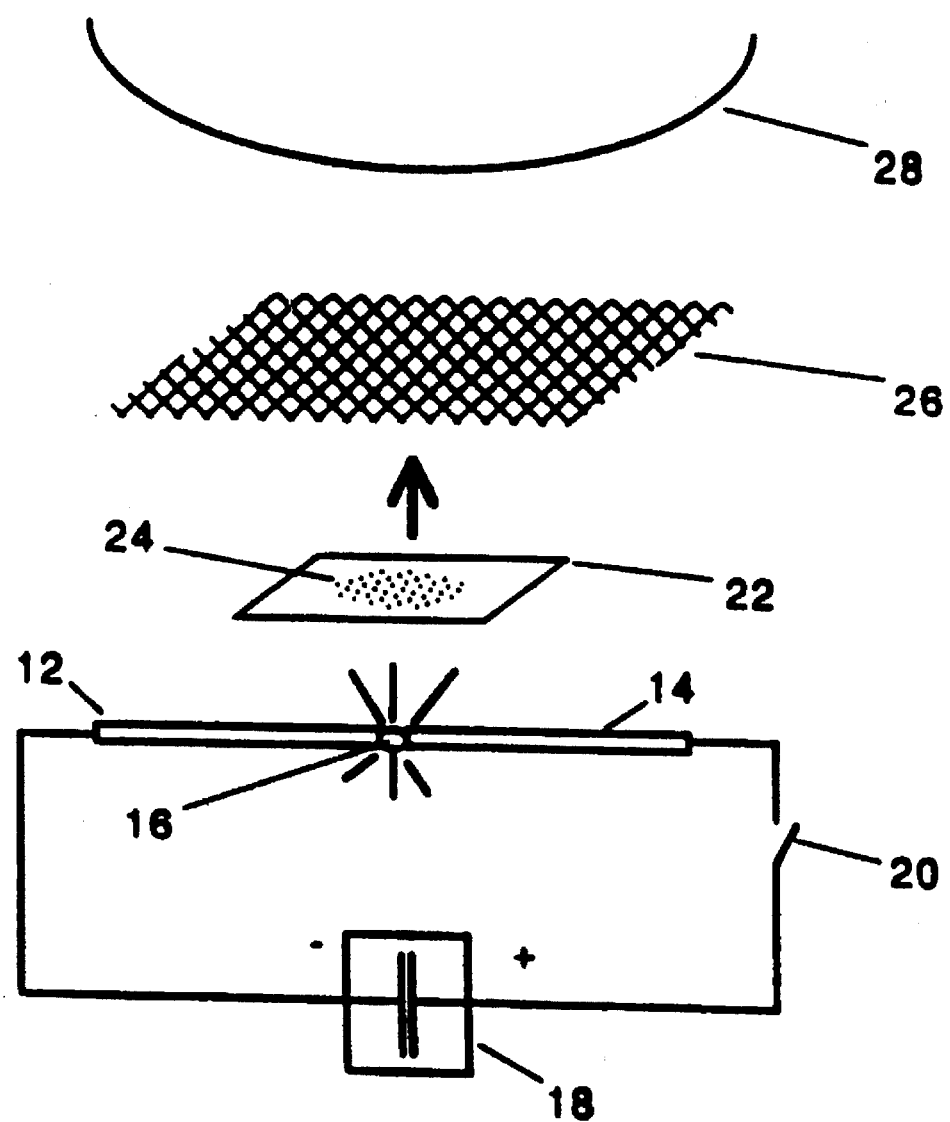
FIG. 8 is a schematic illustration of the method of operation of the instrument of FIG. 1.

Illustrated in FIG. 8 is a schematic illustration intended to illustrate the general method of operation of a particle acceleration genetic transformation device operating on the principal of the preferred embodiment here. As shown in FIG. 8, a pair of electrodes 12 and 14 are provided spaced apart with a spark gap distance between them. The spark gap distance is bridged by a drop of water 16. The end of each of the electrodes 12 and 14 is electrically connected to one terminal of a high voltage capacitor 18, with one of the terminals being connected through a switch 20. After the capacitor 18 is charged and when the switch 20 is closed, high voltage electrical energy is transferred from the capacitor 18 to create a potential between the electrodes 12 and 14. If the potential is sufficiently high, in the order of several kilovolts, a spark will bridge the gap between the electrodes 12 and 14. The electrical spark bridging the electrodes 12 and 14 instantly vaporizes the water droplet 16. The expanding gaseous shock wave created by the instant vaporization of the water droplet 16 propagates radially outward in all directions. Previously placed within the zone which is affected by the shockwave is a carrier sheet 22. The carrier sheet 22 has previously been coated with a number of tiny carrier particles 24. The carrier particles 24 are of very dense material, preferably a metal such as gold, and are of an extremely small size, on the order of a fraction to a few microns in size. The carrier particles 24 are of biologically inert dense material so that they will readily retain momentum and are sufficiently small sized so that they are small in relation to the cells of the organism which they are intended to transform. It has been found that carrier particles of a size of a few microns can enter living cells, by penetrating the cell walls thereof, without adversely affecting the ability of most of the living cells to survive. In other words, the carrier particles can enter living cells without killing them. The carrier particles in an apparatus, such as that shown in FIG. 8, are coated with a genetic construct, typically DNA or RNA, which is intended to be inserted into the living cells of the target organism. At some frequency, the genetic construct delivered by the carrier particles will be expressed in the targeted cells.

In the general scheme of the apparatus of FIG. 8, the carrier sheet 22 is propelled upward by the expanding shock wave from the vaporization of the water droplets 16. The carrier sheet travels upward until it impacts a retaining screen 26 which, as its name implies, is simply a rigid metallic screen intended to retain the carrier sheet 22. When the carrier sheet 22 hits the retaining screen 26, it stops. However, the momentum of movement of the carrier sheet 22, with the carrier particles 24 thereon, is retained by the carrier particles 24, and the carrier particles 24 therefore fly upward from the retaining screen 26 into the target organism 28. The target organism is the biological organism, tissue or cell culture into which it is desired to transfer the genetic material coated onto the carrier particles 24.

It has been previously found that an electric spark discharge transformation apparatus, operating in accordance with the methodology of FIG. 8, has been capable of achieving both somatic cell and germ line transformation of a variety of living organisms from a variety of classes in both the plant and animal kingdoms. For example, the above-mentioned U.S. Pat. Nos. 5,120,657 and 5,149,655 describe earlier electric spark discharge gene delivery instruments used to transform soybean. The instruments have also been successfully applied to the transformation of woody plant species, plant and animal cells in culture, callus cultures of a wide variety of plants, and animal tissues, both intact (i.e. in vivo) and dissected tissues, and both somatic and germ line cells.

In further developing the technology of particle-mediated transformation of cells, one of the areas of inquiry has been toward the somatic transformation of various cell types of larger organisms, such as intact plants or animals. The particle-mediated transformation apparatus disclosed in U.S. Pat. No. 5,120,657 may be used for large organisms, but is not convenient, due to the fact that the apparatus is large and fixed in character. It is sometimes difficult to maneuver a large organism, be it plant or animal, into a location at which it can be transformed by a fixed particle acceleration device.

Using the basic principle of operation illustrated in FIG. 8, the present invention is directed to improving the rate at which particle acceleration treatment process may be performed. In so doing, it provides a convenient apparatus which facilitates preparation of each sample by providing for sample holding components that are easily replaced.

While the preferred embodiment of the apparatus is a hand-held device for particle acceleration, the invention is not so limited. Rather, the invention may be incorporated into any such device in which the sample delivery components are replaced after each sample in accordance with the apparatus disclosed herein.

While the particle acceleration apparatus of the present embodiment utilizes an electric spark discharge, other instruments for accelerated-particle transformation have been designed which operate, for example, by explosive discharge of compressed gas. The expanding compressed gas in such an instrument operates analogously to the shock wave and pressure wave of the instrument illustrated herein in accelerating a carrier sheet toward a target surface. Accordingly, the present invention is therefore not limited to a device which generates a gaseous discharge by electric spark, but rather the present invention may be incorporated into any particle-acceleration device which directs a carrier sheet coated with particles into a retaining screen.

As noted above, the shock wave has sufficient force to lift and accelerate the carrier sheet 22 toward the target sample. Beyond that initial burst, however, it is desirable to redirect any subsequent energy, referred to herein as the "pressure wave" or "excess pressure," away from the target sample. Excess pressure could damage delicate target tissues.

Shown in FIG. 1 is a hand-held particle acceleration apparatus 30 constructed in accordance with the present invention, viewed from the side. The apparatus 30 includes a handle 32 for gripping by the user. The handle 32 is preferably elongated, and can be of any suitable shape or size adapted to the needs of the particular user of the instrument. The handle 32 preferably includes a series of longitudinal bores therethrough. By forming the conduits into the handle, the hand-held apparatus is more conveniently operated, in that the user need not contend with a set of unwieldy tubes and wires interfering with the operative end of the hand-held device. A pair of handle bores 34 through the handle 32 are conduits for electric wires (one such bore is illustrated in dashed lines in FIG. 1). A third handle bore 36 opens to the ambient atmosphere and is intended to draw fumes away from the instrument and into a vacuum system, after discharge. A fourth handle bore 38 acts as a conduit for helium gas through the handle and body member 40 and thus into cartridge holder 72. The handle bore 38, which appears to parallel the handle bore 34 in FIG. 1, is actually located in the centerline of the handle 32, while the two handle bores 34 for the wiring are located on either side of it. Obviously, handle bore configurations other than those described below may be more appropriate if discharge is achieved by means other than electric discharge as shown.

The body member 40, formed as an extension of the handle 32, or attached to one end of the handle 32, is the portion of the instrument in which particle accelerating force is generated. Regardless of how the handle 32 and body member 40 are formed, the bores of the handle 32 extend far enough into the body member 40 to make the electrical, gas, and vacuum connections described herein.

In the preferred embodiment, the accelerating force is generated in a spark discharge chamber 42, which is formed within the body member 40. The spark discharge chamber actually includes a longer rectangular subchamber 44 and a shorter rectangular subchamber 46 joined by a top subchamber 48 to form an inverted J-shaped channel within the body member 40. As shown in FIG. 1, the longer subchamber 44 extends through the body member 40 from bottom to top. The top subchamber 48 extends from the longer subchamber 44 to the shorter subchamber of the spark discharge chamber, and is formed as a rectangular channel along the top of the body member 40. The shorter subchamber 46 does not extend through to the bottom of the body member 40, but rather extends from the top of body member 40 only about halfway into the interior of the body member 40. Between the longer and shorter subchambers 44 and 46 is a baffle 50 which partially separates the two. Positioned within the shorter subchamber 46 of the discharge chamber 42, extending inward from the side edges of the body member 40 at approximately the same height as the distal end of the baffle 50, are apertures containing spark discharge electrodes 52 and 54, as shown in FIG. 2. The ends of the electrodes 52 and 54 are spaced apart by the distance which forms the spark gap between the electrodes. The electrodes themselves are simple cylinders of durable metallic material, such as steel or tungsten alloys. Electrode holders 56 which secure the electrodes 52 and 54 in the electrode apertures are embedded in the sides of the body member 40. Adjustable set screws 57 are provided which extend to the electrode holders 56 in bores provided for them, and are positioned so that electrode position may be adjusted by loosening, and fixed by tightening, the set screws. Access to the electrodes is by side covers 59 which are removably secured to the body member 40 by screws or similar means.

A body cap 58 covers the top of body member 40, including the top subchamber 48, of the body member 40, except as noted below. The body cap is formed of a rigid durable material, such as heavy plastic, that can withstand the high pressures generated during discharge.

Pivotally attached to the body cap 58 directly above the smaller subchamber 46 is a hinged door 60 which both provides user access to the electrodes 52 and 54 in the spark discharge chamber 42 and functions to deflect a portion of the energy released at discharge. The hinged door 60 is attached at one of its ends, by a suitable hinge, to the body cap 58. The hinged door 60 is provided, on its outer surface adjacent to the hinge, with a tab 62, which on rotation, fits into a suitably formed recess in the body cap 58. The tab 62 facilitates opening the hinged door 60. In its partially open position, the door 60 helps to deflect discharge gases away from the target sample and out of the apparatus 30. The hinged door is sufficiently large to cover the shorter subchamber entirely when closed.

Along both sides toward the top of the body member 40 are grooves 66 which receive rails 68 formed on a sliding hood 70. The grooves 66 thereby act as a track into which the rails 68 fit so that the sliding hood 70 may be reciprocally moved. When positioned at one end of the track, the sliding hood 70 covers the hinged door 60. Access to the hinged door, and the electrodes under it, is achieved by sliding the sliding hood 70 along the grooves 66 to the other end of the track. Other means for moving the hood into and out of position over the discharge chamber would also be possible. For example, the hood could be removable rather than slidable. The sliding hood 70 may be fashioned of a sturdy material, such as plastic, and formed in an arched manner over the body cap 58, body member 40 and hinged door 60. Beneath the hood 70, there should be sufficient space to allow gases generated during discharge to expand and then to be drawn rearward through the handle vacuum bore 36 which terminates at the chamber defined by the hood 70.

Figure 3:
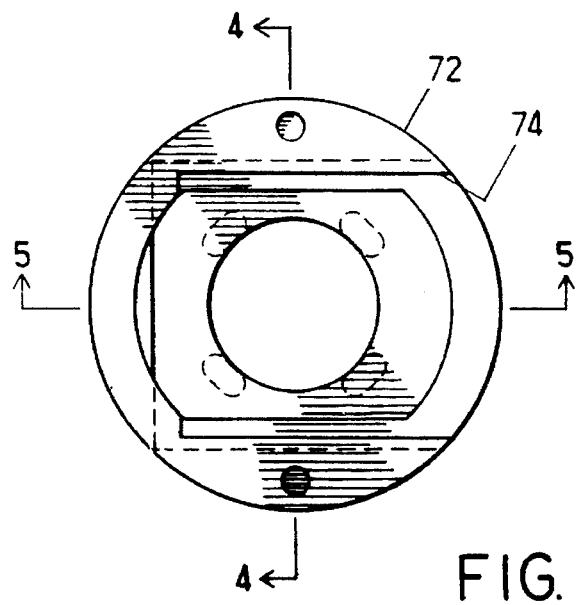
FIG. 3 is a top view of a preferred embodiment of the mounting cartridge holder portion of the apparatus of the present invention.
Figure 4:
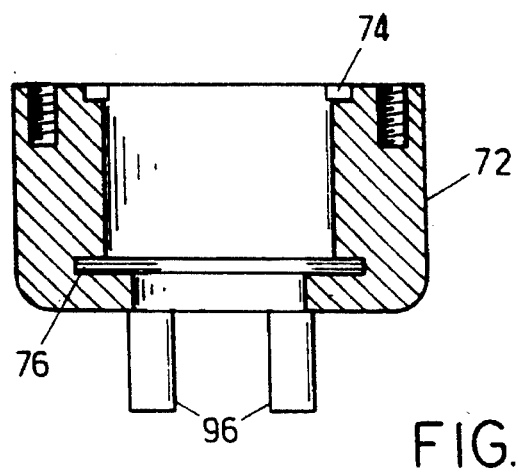
FIG. 4 is a sectional front view of the cartridge holder of FIG. 3.
Figure 5:
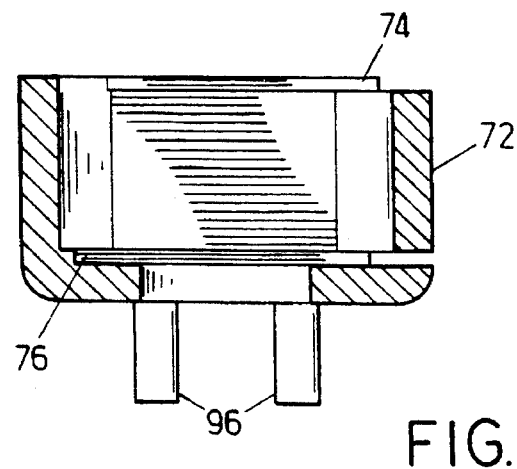
FIG. 5 is a sectional side view of the cartridge holder of FIG. 3.

Connected to the bottom of the body member 40 is a novel cartridge holder 72 for mounting cartridges shown in FIG. 1 and detailed in FIGS. 3–5. The holder 72 is formed of a solid durable material such as metal or plastic, and preferably, though not essentially, is cylindrical, and has an axial bore therethrough. The bore may be any shape, though it too is preferably cylindrical, having an internal volume of approximately 38 cubic centimeters. Therefore, for efficient particle acceleration into a target organism, the bore through the holder 72 is preferably co-axial with the discharge chamber opening through the bottom of the body member 40. The cartridge holder 72 can be itself releasably attached to the body member 40. For example, it may be desirable to replace the cartridge holder 72 itself between patients. Thus the cartridge holder 72 is preferably either disposable or sterilizable.

Most notably, the holder 72 for removable mounting cartridges includes upper and lower apertures, or slots, 74 and 76, respectively, into which mounting cartridges may be removably inserted. The apertures 74 and 76 are provided on planes that are substantially perpendicular to that of the axial bore through the holder 72. The distance between the slots is the distance that an accelerated carrier sheet will travel after being lifted from its resting position during discharge. Accordingly, the distance must be sufficiently great to allow adequate carrier sheet acceleration, but not so great that the carrier sheet is allowed to decelerate appreciably during flight.

Figure 6:
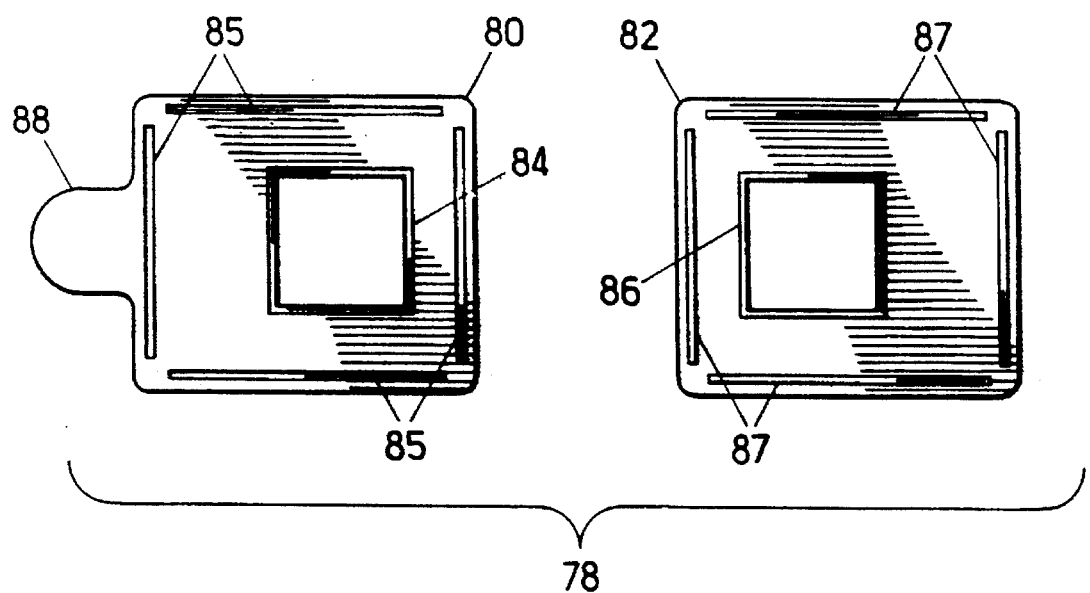
FIG. 6 is an exploded view of a first mounting cartridge for use in the apparatus of the present invention.

In accordance with the present invention, two types of removable mounting cartridges are envisioned for use in the holder 72. A first removable mounting cartridge 78, depicted in FIG. 6 is designed to detachably hold a carrier sheet that has been coated with carrier particles which are themselves coated with biological material. In the preferred embodiment, the cartridge is formed of two substantially rectangular or square upper and lower plates 80 and 82, which mate together to detachably hold the carrier sheet in place. Each of the plates 80 and 82 is provided with a corresponding cut out window just slightly smaller in length and width than the carrier sheet. Around the perimeter of the window on plate 80, a slight recess 84 is provided. On the complementary mating plate 82, the window perimeter is marked by a raised lip 86 having a height approximately equal in magnitude to the depth of the recess 84. Together, the lip 86 and the recess 84 allow the user to easily align the two plates of the first mounting cartridge 78 with the edges of the carrier sheet held between the lip 86 and the recess 84. The first mounting cartridge 78 may be further provided with a tongue 88 on at least one of its halves to facilitate handling and insertion of the cartridge into aperture 74 of the holder 72 by the user. In a preferred embodiment, one plate, such as the upper plate 80, is provided with a series of grooves 85, and the other plate, in this case the lower plate 82, is provided with correspondingly shaped ribs 87. The ribs 87 may be snap fit into the grooves 85 to join the plates 80 and 82 together.

Figure 7:
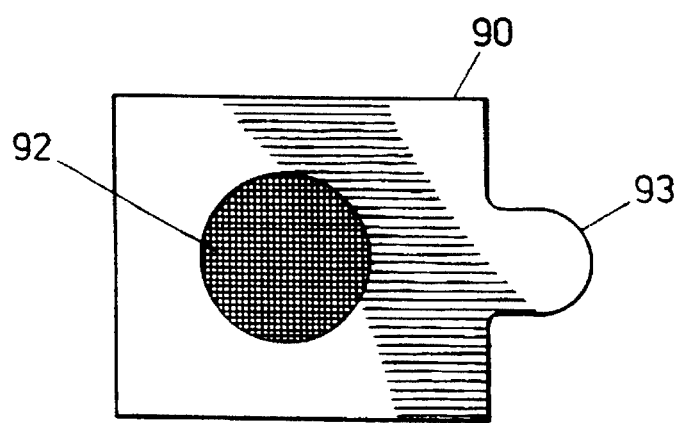
FIG. 7 is a top view of a second mounting cartridge for use in the apparatus at the present invention.

As shown in FIG. 7, the second mounting cartridge 90 comprises a retaining screen 92, and need not be formed of mating portions like the first mounting cartridge. Instead, it may be formed of a single piece of durable material such as plastic or metal, shaped to fit in aperture 76, with provision made to permanently or temporarily receive the retaining screen 92. The retaining screen 92 must not be dislodged after discharge and must remain in position to prevent passage of the carrier sheet from the apparatus 30 into the sample. However, neither the second mounting cartridge 90 nor the retaining screen 92 should prevent passage of the accelerated particles into the sample once they have left the carrier sheet. Therefore, a preferred second mounting cartridge 90 includes the retaining screen 92 molded integrally in an orifice that passes through the cartridge 90, from top to bottom. The second mounting cartridge could also, if desired, be provided with a tongue similar to the tongue 88 of the cartridge 78, as illustrated at 93 in FIG. 7. Like the first mounting cartridge 78, the second mounting cartridge 90 is also reusable after discharge, after the trapped carrier sheet has been removed.

The first removable mounting cartridge 78 is intended to be inserted into the slot 74 closest to the discharge opening at the bottom of body member 40, while the second mounting cartridge 80, bearing the retaining screen, is inserted into the slot 76 located toward the end of the cartridge holder 72 furthest away from the body member 40. Having done so, the inner walls of bore in the holder 72, and the pair of mounting cartridges form a relatively isolated flight chamber across which the accelerated carrier sheet may travel after discharge.

To enhance the efficiency of particle-mediated transformation, the carrier sheet in the first mounting cartridge and the retaining screen in the second mounting cartridge are preferably coaxial. Accurate placement of the two cartridges may be facilitated by forming each to a distinct size and shape and providing correspondingly sized and shaped slots 74 and 76 for each. By doing so, opportunities for operator error are reduced, in that each cartridge will fit only in its proper slot, and will be insertible only in its proper orientation. As noted in the Figures, slot 74 is shorter and narrower than slot 76, which extends further into the holder 72, making it impossible to place a mounting cartridge into the wrong slot. This attention to design also ensures that upon discharge, the carrier sheet will move as desired toward the retaining screen.

It is known that acceleration of the carrier sheet is enhanced by a reduction in atmospheric resistance along the flight path through the chamber. This reduction may be achieved by displacing the ambient air in the flight path with a gas having a lower density than air, such as helium gas. As a further benefit, the decreased atmospheric density in the flight path acts to hinder the propagation of any pressure wave from the discharge chamber to the target animal. Low density gas is preferably provided to the flight chamber via the gas conduit 38 in the handle 32, which extends through the body member 40 as well. It is not essential that the gas port 94 traverse the body member 40. Any means for delivering low density gas to the flight path would be adequate, though ease-of-use is increased by embedding the gas delivery inside the solid members of the apparatus, as shown.

Preferably affixed to the bottom of the cartridge holder 72, as shown in FIG. 1 and FIGS. 3–5, are a plurality of spacing legs 96 of equal length intended to fix a constant, reproducible desired distance between the retaining screen and the target. These spacing legs 96 may be formed of any rigid material, such as plastic and may be sized to accommodate a range of spacing distances.

Because of the great force generated during discharge, it is important that the component parts of the hand-held device 30 be securely fixed to one another. In the preferred embodiment, the body cap 58 and body member 40, are held firmly together by screws sunk through the body cap 58 and into the body member 40. Cartridge holder 72 is readily removable to permit sterilization, if desired. The cartridge holder 72 mounts to body 40 by means of a mating rail and groove configuration. The cartridge holder 72 is maintained in position by two (2) spring plungers (not shown) installed in body 40. The plungers engage small recesses in holder 72 when the cartridge holder 72 is installed. While this arrangement ensures solidity, other means for joining the component parts together also exist. It is preferred that the components can be disassembled for cleaning and repair as needed.

The complete apparatus of the present invention does require a base, or support, unit including relatively non-mobile elements, for power and gas sources, as will be described below. However, the hand manipulable unit as illustrated in FIG. 1 is very light, easy to operate, and can be readily extended and operated on any portion of the target organisms, even those which are relatively difficult to work with or are non-cooperative targets, such as large non-anesthetized animals.

Now the operation of the apparatus 30 of FIG. 1 can be understood in detail. To operate the particle transformation apparatus 30, in addition to the apparatus detailed in FIGS. 1 through 7, there is a source of electric spark discharge voltage, similar to those described in U.S. Pat. Nos. 5,120,657 and 5,149,655. In addition, there is a source of gaseous helium. The power supply circuitry and a storage supply of helium gas are located in a base support unit to which the hand-held instrument of FIG. 1 is attached. The attachment is via handle conduits that includes the appropriate wires to conduct the power from the voltage-generating circuit to the electrodes 52 and 54, a conduit for the helium gas, and conduit for withdrawing fumes from the hand-held apparatus 30 to the vacuum system. The flexible connection allows extensive and easy freedom of movement of the hand-held apparatus 30 throughout the length of the umbilical connection.

To operate the apparatus of FIG. 1 the sliding hood 70 is slid along the track away from the handle to reveal the hinged door 60. The hinged door 60 is pivoted up and away from the body member 40, revealing the discharge chamber 42. A water droplet is placed between the ends of the spark discharge electrodes 52 and 54 in the shorter subchamber 46 of the discharge chamber 42. If the spark discharge gap distance has changed over time, due to variations in the device or wear in the electrodes, the gap between the electrodes can be adjusted readily by letting up on the set screws and adjusting the electrodes 52 and 54 before resetting the set screws. The gap between the electrodes should be approximately 1.27 mm. When the electrodes have been adjusted and the water droplet has been placed between the electrodes, the hinged door 60 is closed again and the sliding hood 70 is slid in the direction of the handle until the hood covers the hinged door 60.

Separately, and preferably previously, copies of the genetic material, either DNA or RNA, which is desired to be inserted into the target organism, have been coated onto carrier particles which in turn are then coated upon the carrier sheet of the type illustrated schematically at 22 in FIG. 8. The carrier sheet for use within the present invention can be any stiff or semi-rigid sheet of light planar material, but is preferably saran-coated aluminized mylar. Before being coated with carrier particles, the carrier sheet is cut to a size that allows it to be seated within the recess 84 of plate 80 of the first mounting cartridge. To secure the carrier sheet in place, plates 80 and 82 of the first mounting cartridge are secured together using the recess 84 and lip 86 to orient the two. The recess 84 and the lip 86 function to position and gently retain carrier sheet in the mounting cartridge. The plates 80 and 82 are held together by an interference fit between the rails 87 and the grooves 85 at the perimeter of the plates 80 and 82. Because it is an object of the present invention to permit rapid sequential treatment, it is preferred that a supply of many such mounted carrier sheets be prepared before performing the accelerated particle transformation procedures, thereby permitting a series of samples to be processed in rapid succession.

To perform the accelerated particle transformation procedure, the first mounting cartridge 78 carrying a detachably mounted carrier sheet is inserted into the holder slot 74. The second mounting cartridge 90 having the retaining screen is inserted into the holder slot 76. A helium flow can then be initiated from the source of gaseous helium, through the gas port 94 into the flight chamber formed by the holder 72 and the mounting cartridges 78 and 90.

The instrument is then ready for use. The apparatus 30 can then be applied close to the target. The spacing legs 96 may contact the target, thereby fixing the distance from the retaining screen. A switch is then thrown, applying the high voltage electric discharge to the electrodes 52 and 54. A spark discharge then jumps between the electrodes 52 and 54, instantly vaporizing the water droplet placed therebetween. The expanding shock wave reverberates throughout the spark discharge chamber 42, but only indirectly impacts the carrier sheet, since the wave must pass around the baffle 50 between the large and small subchambers of the discharge chamber 42 before it reaches the carrier sheet. The carrier sheet is detached from the first mounting cartridge 78 with great force, and is hurled toward the retaining screen 92 in the second mounting cartridge 90. The carrier sheet accelerates until it impacts the retaining screen 92 of the second mounting cartridge 90, and then stops abruptly.

The carrier particles fly off of the carrier sheet and proceed onward into the cells of the target organism. The carrier particles enter the cells of the organism. The genetic material on the carrier particles is thus introduced into the cells of the organism where the genetic material is, at a repeatable frequency, tangentially expressed by the tissues of the target organism and, at a lesser, but known, statistically significant frequency, stably integrated into the genome of the target cells. The target cells can be somatic cells of plant, animal, or any other life form, or, if germline transformation is desired, can be germline cells of the organism.

After the immediate shock wave created by the initial explosive shock urges the carrier sheet to accelerate toward the target, a subsequent strong pressure wave is created from the expanding gases generated during spark discharge. The baffle 50 in the discharge chamber 42 acts to restrict the ability of the pressure wave to propagate toward the carrier sheet. Meanwhile, most of the excess pressure wave exits through the hinged door 60, which pivots open until its distal end contacts the underside of hood 70. Some of the initial plasma generated by the spark passes through the opened door 60 and into the chamber formed by the sliding hood 70 positioned over the door 60. The plasma is then drawn away into the vacuum being drawn through the vacuum bore 36 of the handle 32.

Some pressure in excess of that necessary to lift and accelerate the carrier sheet may pass into the helium-rich flight chamber. However, because the density of the helium in the chamber is low relative to that of an air-filled chamber, such excess pressure does not propagate well and largely dissipates before reaching the target sample.

Following a first discharge, an apparatus containing a holder constructed in accordance with the present invention may quickly be readied for a next discharge simply by replacing the first mounting cartridge 78 with another prepared in advance as described above. Next, the second mounting cartridge 90 may be removed and replaced either with another or with the same cartridge from which the spent carrier sheet has been removed. The second mounting cartridge may be cleaned before reuse by removing all pieces of the carrier sheet and washing. Finally, a new water droplet is placed between the electrodes as described above.

Accordingly, in short order, the apparatus is ready again for particle acceleration. This is in marked contrast to earlier particle acceleration devices in which it was necessary to disassemble the device for removal of the used carrier sheet and to secure a new carrier sheet in place. Whereas it was not previously necessary to process several samples in rapid succession, this need has grown more acute as use of the accelerated particle technology has expanded to include large, often uncooperative, animals. Moreover, as it is envisioned that this technology will ultimately be useful for routine delivery of human genetic vaccines, it is desirable that delivery time per patient be minimized, particularly for use in large-scale immunization programs, in much the same way disposable injection cartridges are used today.

We claim:

1. An apparatus for acceleration of carrier particles into a target organism, the carrier particles being coated with biological material and being initially loaded onto a carrier sheet, the apparatus comprising:

a body member having a discharge chamber formed in its interior, the discharge chamber having first and second openings into two sides of the body member;

a first mounting cartridge comprising an upper plate and a lower plate, each plate having a window therethrough, each window being smaller than the carrier sheet, the plates being adapted for mating together and detachably holding the carrier sheet in the windows;

a cartridge holder having an axial bore therethrough and having a first aperture adapted for removable insertion of the first mounting cartridge, the holder having a second aperture adapted for removable insertion of a second mounting cartridge comprising a retaining screen, the first aperture being substantially parallel to the second aperture, the apertures being substantially perpendicular to the axial bore, the holder being attached to the body member such that the axial bore is adjacent to the first opening; and means for generating a gaseous shock wave in the discharge chamber.

2. An apparatus as claimed in claim 1 wherein the discharge chamber is an electric spark discharge chamber and wherein the means for generating a gaseous shock wave comprises a pair of electrodes removably mounted within the discharge chamber and a power source attached to the electrodes for causing a spark discharge and gaseous shock wave in the discharge chamber.

3. An apparatus as claimed in claim 1 wherein the body member has a gas port that directs a gas that is less dense than air into the axial bore.

4. An apparatus as claimed in claim 1 further comprising a hinged door pivotally mounted to the body member above the second opening such that it pivots out of the way to open the second opening after the shock wave is generated to vent excess pressure away from the target organism.

5. An apparatus as claimed in claim 1 further comprising a hood movably mounted to the body member in communication with the second opening so that the hood contains gases generated in the discharge chamber.

6. An apparatus as claimed in claim 1 further comprising a handle connected to the body member, the handle having one or more longitudinal bores therethrough extending into the body member.

7. A mounting cartridge adapted for use in an apparatus for accelerating carrier particles into a target organism, the carrier particles coated with biological material and initially loaded onto a carrier sheet, the apparatus comprising a holder for removable mounting cartridges, the mounting cartridge comprising an upper plate and a lower plate, each plate having a window therethrough, each window being smaller than the carrier sheet, the plates being adapted for mating together and detachably holding the carrier sheet in the windows, the cartridge being removably insertible into the holder.

8. A method for acceleration of carrier particles into a target organism, the carrier particles coated with biological material and initially loaded onto a carrier sheet, the method comprising:

providing an apparatus comprising a body member having a discharge chamber formed in its interior, the discharge chamber having first and second openings into two sides of the body member, a first mounting cartridge comprising an upper plate and a lower plate, each plate having a window therethrough, each window being smaller than the carrier sheet, the plates being adapted for mating together and detachably holding the carrier sheet in the windows, a holder for removable mounting cartridges attached to the body member at a position adjacent to one of the openings, the holder having an axial bore therethrough and having a first aperture adapted for removable insertion of the first mounting cartridge, the holder having a second aperture adapted for removable insertion of a second mounting cartridge comprising a retaining screen, the first aperture being substantially parallel to the second aperture, the apertures being substantially perpendicular to the axial bore, the holder being attached to the body member such that the axial bore is adjacent to the first opening, and means for generating a gaseous shock wave in the discharge chamber;

detachably mounting the carrier sheet onto the first mounting cartridge;

inserting the first mounting cartridge into the first aperture;

inserting the second mounting cartridge into the second aperture; and generating a gaseous shock wave in the discharge chamber.

9. A method as claimed in claim 8 wherein the discharge chamber is an electric spark discharge chamber and wherein the means for generating a gaseous shock wave comprises a pair of electrodes removably mounted within the discharge chamber and a power source attached to the electrodes for causing a spark discharge and gaseous shock wave in the discharge chamber.

10. A method as claimed in claim 8 wherein the body member has a gas port that directs a gas that is less dense than air into the axial bore.

11. A method as claimed in claim 8 wherein the apparatus further comprises a hinged door pivotally mounted to the body member above the second opening such that it pivots out of the way to open the second opening after the shock wave is generated to vent excess pressure away from the target organism.

12. A method as claimed in claim 8 wherein the apparatus further comprises a hood movably mounted to the body member in communication with the second opening so that the hood contains gases generated in the discharge chamber.

13. A method as claimed in claim 8 wherein the apparatus further comprises a handle connected to the body member, the handle having one or more longitudinal bores therethrough extending into the body member.

* * * * *